(12) United States Patent
Mishima

(10) Patent No.: US 10,379,064 B2
(45) Date of Patent: Aug. 13, 2019

(54) SUBSTRATE INSPECTION DEVICE AND SUBSTRATE MANUFACTURING METHOD

(71) Applicant: NIPPON MEKTRON, LTD., Tokyo (JP)

(72) Inventor: Kenichi Mishima, Tokyo (JP)

(73) Assignee: NIPPON MEKTRON, LTD., Tokyo (JP)

(*) Notice: Subject to any disclaimer, the term of this patent is extended or adjusted under 35 U.S.C. 154(b) by 302 days.

(21) Appl. No.: 15/535,775

(22) PCT Filed: Dec. 16, 2016

(86) PCT No.: PCT/JP2016/087670
§ 371 (c)(1),
(2) Date: Jun. 14, 2017

(87) PCT Pub. No.: WO2017/216986
PCT Pub. Date: Dec. 21, 2017

(65) Prior Publication Data
US 2018/0202946 A1 Jul. 19, 2018

(30) Foreign Application Priority Data

Jun. 13, 2016 (JP) ................................. 2016-117269

(51) Int. Cl.
*G06K 9/00* (2006.01)
*G01N 21/956* (2006.01)
(Continued)

(52) U.S. Cl.
CPC ....... *G01N 21/95684* (2013.01); *B32B 15/08* (2013.01); *B32B 27/34* (2013.01);
(Continued)

(58) Field of Classification Search
CPC .. G01N 21/956; G01N 21/95684; G06T 7/32; G06T 7/13; B32B 15/08; B32B 27/34; G01B 11/24; H05K 3/285
See application file for complete search history.

(56) References Cited

U.S. PATENT DOCUMENTS 8,482,728 B2 * 7/2013 Uto .................... G01N 21/9501
356/237.4
8,692,344 B2 * 4/2014 Oganesian ............ H04N 5/374
257/431
(Continued)

FOREIGN PATENT DOCUMENTS

JP 2002-296016 A 10/2002
JP 2006-118896 A 5/2006
(Continued)

OTHER PUBLICATIONS

International Search Report issued in PCT/JP2016/087670; dated Mar. 14, 2017.

*Primary Examiner* — Gregory M Desire
(74) *Attorney, Agent, or Firm* — Studebaker & Brackett PC

(57) ABSTRACT

A substrate inspection device for inspecting a flexible printed board to determine whether the transparent adhesive material is properly applied thereto comprises: a substrate reading device which irradiates the flexible printed board with visible light to acquire image data; an adhesive material position determination unit which determines a position of adhesive material CAD data corresponding to the transparent adhesive material with respect to blue color image data among the image data corresponding to blue light which is readily absorbed by polyimide, to create adhesive material alignment data in which the adhesive material CAD data is superposed; an edge enhancing unit which performs processing, on the blue color image data, to enhance an edge of
(Continued)

the transparent adhesive material; and a straight line determination unit which determines whether the edge of the transparent adhesive material is present in edge enhanced data in which the edge of the transparent adhesive material is enhanced.

15 Claims, 6 Drawing Sheets

(51) Int. Cl.

| | |
|---|---|
| *B32B 15/08* | (2006.01) |
| *B32B 27/34* | (2006.01) |
| *G06T 7/32* | (2017.01) |
| *G01B 11/24* | (2006.01) |
| *G06T 7/00* | (2017.01) |
| *H05K 3/28* | (2006.01) |
| *G06T 5/00* | (2006.01) |
| *G06T 7/13* | (2017.01) |
| *H05K 1/02* | (2006.01) |

(52) U.S. Cl.
CPC ........... *G01B 11/24* (2013.01); *G01N 21/956* (2013.01); *G06T 5/004* (2013.01); *G06T 7/001* (2013.01); *G06T 7/13* (2017.01); *G06T 7/32* (2017.01); *H05K 3/285* (2013.01); *G06T 2207/10024* (2013.01); *G06T 2207/20061* (2013.01); *G06T 2207/20192* (2013.01); *G06T 2207/30141* (2013.01); *H05K 1/0269* (2013.01); *H05K 2203/161* (2013.01); *H05K 2203/162* (2013.01)

(56) References Cited

U.S. PATENT DOCUMENTS

| | | | |
|---|---|---|---|
| 8,876,352 B2* | 11/2014 | Robbins | .................... F21K 9/00 |
| | | | 362/612 |
| 2004/0264759 A1 | 12/2004 | Hattori et al. | |
| 2009/0114426 A1 | 5/2009 | Tsunekawa et al. | |
| 2016/0209637 A1* | 7/2016 | Fujimori | ................ A61B 1/051 |
| 2016/0322437 A1* | 11/2016 | Sakamoto | ........... H01L 27/3246 |
| 2018/0202946 A1* | 7/2018 | Mishima | ................... G06T 7/32 |

FOREIGN PATENT DOCUMENTS

| | | |
|---|---|---|
| JP | 2009-117572 A | 5/2009 |
| JP | 2009-175150 A | 8/2009 |
| JP | 2010-217169 A | 9/2010 |
| JP | 2010-281580 A | 12/2010 |
| TW | 200922397 A | 5/2009 |

* cited by examiner

SUBSTRATE INSPECTION DEVICE AND SUBSTRATE MANUFACTURING METHOD

TECHNICAL FIELD

The present invention relates to a substrate inspection device and a substrate manufacturing method.

BACKGROUND ART

In the process of manufacturing a product, a surface of a sheet member, such as a substrate, is often provided with covering material by applying a separate member to the sheet member or by coating the sheet member. The covering material is often inspected manually. Inspection techniques involving no human intervention are disclosed in Patent Document 1 and Patent Document 2, for example.

In Patent Document 1, in order to inspect an object to be inspected of which a surface is covered with a coating that emits fluorescence upon ultraviolet light irradiation, an ultraviolet light image is created based on irradiation using an ultraviolet light source, and a visible light image is created based on irradiation using a visible light source. Based on the visible light image, a position identification unit identifies position information of the object to be inspected. Based on the identified position information of the object to be inspected and the ultraviolet light image, the coating on the object to be inspected is inspected.

In Patent Document 2, in order to inspect whether a printed board is properly coated with desiccant, the desiccant is provided with a fluorescence agent which emits fluorescence. An ultraviolet radiation unit irradiates the printed board with ultraviolet light, and the printed board is photographed by a photographing unit. In a reference information storage unit, reference information concerning regions to be coated with desiccant is stored. Based on an image obtained by the photographing unit, a determination unit determines whether the desiccant is coated in the regions to be coated with desiccant, using the results of comparison of the brightness of an image of a region including a fluorescence region and a predetermined threshold value, and the reference information.

CITATION LIST

Patent Document

Patent Document 1: JP-A-2009-175150
Patent Document 2: JP-A-2010-281580

SUMMARY OF INVENTION

Problems to be Solved by the Invention

In a flexible printed board including a polyimide base member with a circuit pattern of copper foil formed by etching, for example, a clear adhesive material (transparent adhesive material) may be applied on a surface. The adhesive material is formed in a prescribed shape in accordance with the position where the circuit pattern and the like is formed. In addition, the position on the base member where the adhesive is to be applied is in many cases prescribed by the positioning and the like of the circuit pattern.

Inspection for failures, such as misaligned application or forgotten application of the transparent adhesive material on the flexible printed board, is typically visually conducted. However, a transparent adhesive material is often difficult to visually distinguish, resulting in an increase in inspection errors. Making the inspection more stringent to prevent inspection error may lead to the problem of an increase in the number of inspection steps.

Accordingly, it is preferable to be able to automatically determine whether the transparent adhesive material has been normally applied, rather than by visual inspection. For this purpose, it may be contemplated to apply the techniques disclosed in Patent Document 1 and Patent Document 2 to detect whether a transparent adhesive material is normally applied.

However, in the configurations disclosed in Patent Document 1 and Patent Document 2, a coated region including fluorescence agent is irradiated with ultraviolet light. The configurations, therefore, are difficult to be applied for a transparent adhesive material that does not include fluorescence agent. In addition, in the configurations disclosed in Patent Document 1 and Patent Document 2, the devices require an ultraviolet light source and the like, making the configurations complicated and costly.

The present invention was made in view of the above circumstances. An object of the present invention is to provide a substrate inspection device and a substrate manufacturing method set forth below. With the substrate inspection device and the substrate manufacturing method, it can be satisfactorily determined, using a relatively simple configuration, whether a transparent adhesive material is properly applied on a base member.

Solutions to the Problems

In order to solve the above problem, according to the first viewpoint of the present invention, a substrate inspection device is provided. The substrate inspection device inspects a flexible printed board including a base member made of polyimide material and a transparent adhesive material applied thereto to determine whether the transparent adhesive material is properly applied. The substrate inspection device includes: a substrate reading device that irradiates the flexible printed board with visible light to acquire image data of the flexible printed board; an adhesive material position determination unit that determines a position of adhesive material CAD data corresponding to the transparent adhesive material, with respect to blue color image data among the image data corresponding to blue light that is readily absorbed by the polyimide; an edge enhancing unit that performs processing, on image data including at least the blue color image data, to enhance an edge of the transparent adhesive material; and a straight line determination unit that determines whether, based on edge enhanced data in which the edge of the transparent adhesive material has been enhanced by the edge enhancing unit, the edge of the transparent adhesive material is present in the edge enhanced data.

Furthermore, other aspect of the present invention is as follows. In the above mentioned invention, preferably, the substrate inspection device includes a binarization processing unit that creates binary image data by performing binarization processing on the edge enhanced data in which the edge of the transparent adhesive material has been enhanced by the edge enhancing unit and the straight line determination unit determines whether, based on the binary image data, the edge of the transparent adhesive material is present.

Furthermore, other aspect of the present invention is as follows. In the above mentioned invention, preferably, the substrate inspection device includes an adhesive material edge cut-out unit that forms a cut-out image by, after the position determination by the adhesive material position determination unit, cutting out image data in an area of a predetermined distance from an edge of the adhesive material CAD data, based on adhesive material alignment data in which the adhesive material CAD data is superposed on the blue color image data, and the edge enhancing unit performs processing to enhance the edge of the transparent adhesive material based on the cut-out image.

Furthermore, other aspect of the present invention is as follows. In the above mentioned invention, preferably, the substrate inspection device includes a rotation processing unit that rotates the cut-out image formed by the adhesive material edge cut-out unit so that a long side of the cut-out image which is parallel or vertical with respect to the edge of the adhesive material CAD data becomes horizontal or vertical with respect to a reference coordinate axis, and the edge enhancing unit performs processing to enhance the edge of the transparent adhesive material based on the cut-out image after the rotation processing.

Furthermore, other aspect of the present invention is as follows. In the above mentioned invention, preferably, the straight line determination unit detects, by the Hough transform, whether a straight line corresponding to the edge of the transparent adhesive material is present, and, after the straight line detection, determines that the edge of the transparent adhesive material is present if pixels having a pixel value indicating an edge are present on the straight line by a predetermined ratio or more.

Furthermore, according to the second viewpoint of the present invention, a substrate inspection device is provided. The substrate inspection device inspects a flexible printed board including a base member made of polyimide material and a transparent adhesive material applied thereto to determine whether the transparent adhesive material is properly applied. The substrate inspection device includes: a substrate reading device that irradiates the flexible printed board with visible light to acquire image data of the flexible printed board; an adhesive material position determination unit that determines a position of adhesive material CAD data corresponding to the transparent adhesive material with respect to blue color image data among the image data corresponding to blue light that is readily absorbed by the polyimide, and that, after the determination, creates adhesive material alignment data in which the adhesive material CAD data is superposed; an expansion processing unit that forms a mask region by performing expansion processing to outwardly expand each side of element data of each transparent adhesive material in the adhesive material CAD data, just by a predetermined size; an edge enhancing unit that, by performing binarization processing while enhancing an edge of the transparent adhesive material or foreign matter on the image data outside an area of the mask region, extracts the edge of the transparent adhesive material or the edge of foreign matter; and an adhesive material determination unit that, based on edge enhanced data in which the edge of the transparent adhesive material or the foreign matter has been enhanced by the edge enhancing unit, determines whether the edge of the transparent adhesive material or the edge of foreign matter is present outside an area expanded by the expansion processing unit.

Furthermore, according to the third viewpoint of the present invention, a substrate manufacturing method is provided. The substrate manufacturing method is for manufacturing a flexible printed board including a base member made of polyimide material and a transparent adhesive material applied thereto. The method includes: a substrate reading step of irradiating the flexible printed board with visible light, and acquiring image data of the flexible printed board; an adhesive material position determination step of determining a position of adhesive material CAD data corresponding to the transparent adhesive material with respect to blue color image data among the image data corresponding to blue light that is readily absorbed by the polyimide; an edge enhancement step of performing processing, on image data including at least the blue color image data, to enhance an edge of the transparent adhesive material; a binarization processing step of extracting the edge of the transparent adhesive material by creating binary image data by performing binarization processing on the edge enhanced data in which the edge of the transparent adhesive material has been enhanced by the edge enhancing unit; and a straight line determination step of determining, based on the binary image data, whether the edge of the transparent adhesive material is present in the binary image data.

Furthermore, according to the third viewpoint of the present invention, a substrate manufacturing method is provided. The substrate manufacturing method is for manufacturing a flexible printed board including a base member made of polyimide material and a transparent adhesive material applied thereto. The method includes: a substrate reading step of irradiating the flexible printed board with visible light, and acquiring image data of the flexible printed board; an adhesive material position determination step of determining a position of adhesive material CAD data corresponding to the transparent adhesive material with respect to blue color image data among the image data corresponding to blue light that is readily absorbed by the polyimide; an expansion processing step of forming a mask region by performing expansion processing so as to outwardly expand each side of element data of each transparent adhesive material in the adhesive material CAD data just by a predetermined size; an edge enhancement step of extracting, by performing binarization processing while enhancing an edge of the transparent adhesive material or foreign matter on the image data outside an area of the mask region, the edge of the transparent adhesive material or the edge of foreign matter; and an adhesive material determination step of determining, based on edge enhanced data in which the edge of the transparent adhesive material or the foreign matter has been enhanced by the edge enhancement step, whether the edge of the transparent adhesive material or the edge of foreign matter is present outside an area expanded by the expansion processing step.

Effects of the Invention

According to the present invention, it can be satisfactorily checked using a relatively simple configuration whether a transparent adhesive material is properly applied on a base member.

DESCRIPTION OF EMBODIMENTS

In the following, a substrate inspection device 10 and a substrate manufacturing method according to an embodiment of the present invention will be described with reference to the drawings. Before a description of the substrate inspection device 10, the configuration of a flexible printed board 100 as the object to be inspected will be described, and thereafter the substrate inspection device 10 and the substrate manufacturing method will be described.

1. Configuration of Flexible Printed Board

Figure 1:
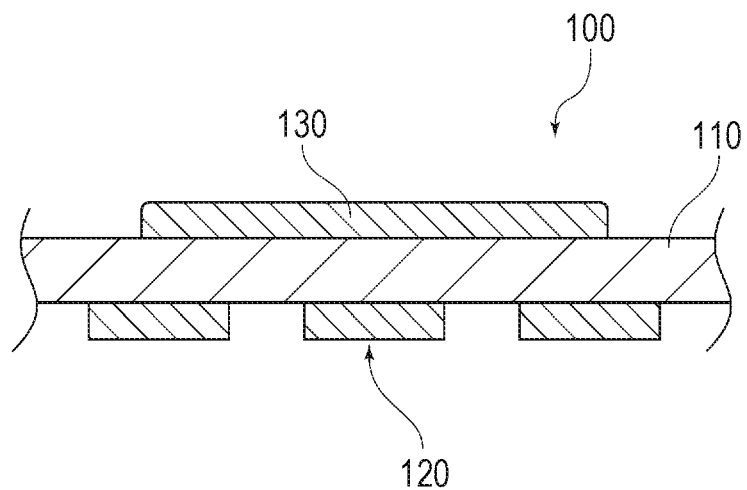
FIG. 1 is a cross-sectional view illustrating a configuration of a flexible printed board according to an embodiment of the present invention.

FIG. 1 is a cross-sectional view illustrating a configuration of the flexible printed board 100 according to the present embodiment. As illustrated in FIG. 1, the flexible printed board 100 of the present embodiment is provided with a base member 110, a circuit pattern 120, and a transparent adhesive material 130. The base member 110 is made of polyimide and has a predetermined thickness. The base member 110 is in a state of appearing a yellow-based color despite having transparency. That is, polyimide, due to its molecular structure, absorbs light having shorter wavelengths, i.e., blue light and ultraviolet light. For this reason, the base member 110 is in the state of appearing a yellow-based color.

The yellow-based color may include yellow, orange, brown, and mixtures thereof. The base member 110 has a front surface that can reflect light having a wavelength in a range of from 570 nm to 620 nm.

The circuit pattern 120 is provided on a back surface side of the base member 110. The circuit pattern 120 is the portion formed by, e.g., patterning a metal foil, such as a copper foil, in a desired pattern shape using a conventional photofabrication technique, such as etching.

The transparent adhesive material 130 is applied to the front surface side of the base member 110. The transparent adhesive material 130 is a sheet member having adhesiveness and formed in a predetermined pattern shape. The transparent adhesive material 130 also has transparency to transmit visible light.

The transparent adhesive material 130 may be any material as long as it has transparency and has adhesiveness on both sides thereof. For example, adhesive layers may be provided on both sides of a polyimide film of polyimide material which is significantly thinner than the base member 110. In this case, the polyimide film appears a yellow-based color. Because the polyimide film is significantly thinner than the base member 110, the absorption of blue light and ultraviolet light is decreased. In this case, the polyimide film can be handled in the same way as if not colored in a yellow-based color.

Figure 2:
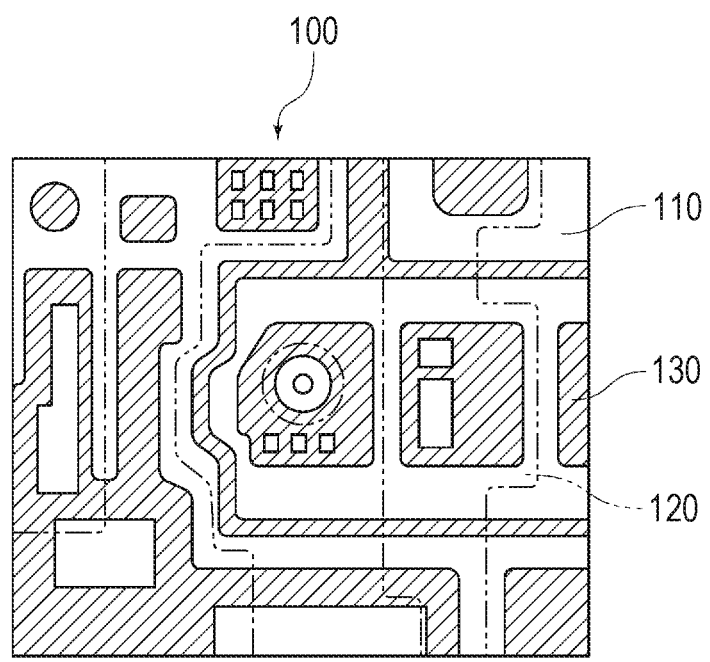
FIG. 2 is a partial front view of the flexible printed board according to the embodiment of the present invention.

FIG. 2 is a partial front view of the flexible printed board 100 according to the present embodiment. In FIG. 2, dashed-and-double-dotted lines indicate the contours of the transparent adhesive material 130. Hatched portions indicate the circuit pattern 120 as viewed through the base member 110. As illustrated in FIG. 2, the position where the transparent adhesive material 130 is to be applied to the base member 110 is determined in advance in accordance with the pattern shape of the circuit pattern 120.

In the substrate inspection device 10, as will be described later, an inspection is performed as follows. First, it is checked whether the transparent adhesive material 130 is applied at the correct position with respect to the pattern shape of the circuit pattern 120. If the transparent adhesive material 130 is not applied at the correct position with respect to the circuit pattern 120, this may include the case where the position of the transparent adhesive material 130 relative to the circuit pattern 120 is displaced, and another case. In the latter case, although the transparent adhesive material 130 is applied at the correct position with respect to the circuit pattern 120 at a predetermined position on the flexible printed board 100, the transparent adhesive material 130 has a position error with respect to the circuit pattern 120 at another specific position due to differences in expansion or contraction between the circuit pattern 120 and the transparent adhesive material 130, or due to bending.

The substrate inspection device 10 is also used to determine whether the contour (edge) of the transparent adhesive material 130 is present outside the correct area or portion for application, and whether foreign matter is attached on the base member 110.

2. Configuration of Substrate Inspection Device

Figure 3:
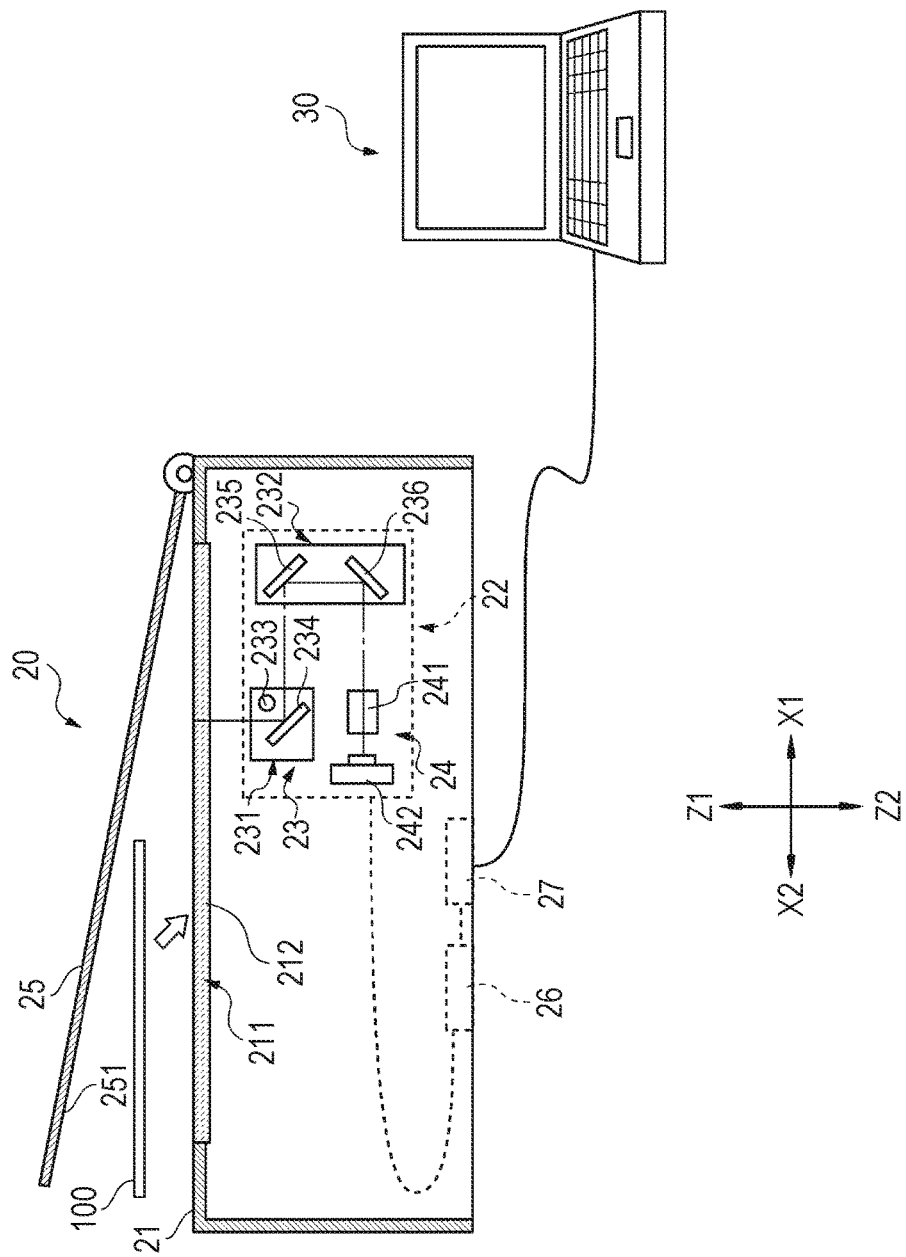
FIG. 3 is a schematic view illustrating a configuration of a substrate inspection device according to the embodiment of the present invention.

The substrate inspection device 10 for inspecting the flexible printed board 100 for position error and foreign matter will be described. FIG. 3 is a schematic view illustrating a configuration of the substrate inspection device 10. As illustrated in FIG. 3, the substrate inspection device 10 is provided with a substrate reading device 20 and a computer 30.

In the case where the substrate reading device 20 is provided with the function of the computer 30, the separate computer 30 may not be required. In this case, the substrate reading device 20 may singly function as the substrate inspection device 10. The configuration of the substrate reading device 20 which will be described with reference to FIG. 3 is an example of the substrate reading device. The substrate reading device may include other configurations.

<2-1. Substrate Reading Device>

As illustrated in FIG. 3, the substrate reading device 20 includes a housing 21, a movable member 22, a lid 25, a control unit 26, and an interface 27. The housing 21 has an opening portion 211. To the opening portion 211, a photographing base 212 made of a transparent member of glass and the like is mounted. When reading the flexible printed board 100 on the photographing base 212, the flexible printed board 100 is placed one by one. Alternatively, a plurality of flexible printed boards 100 may be placed without overlapping each other.

In the housing 21, the movable member 22 is disposed in a movable state. Specifically, in the housing 21, a motor which is not illustrated is provided. The motor is driven to move the movable member 22 via a transmission mechanism which, while not illustrated, may include gears and belts, in X-directions while being guided by a guide member, which is not illustrated.

The movable member 22 includes an optical unit 23 and a data conversion unit 24. Of these, the optical unit 23 includes an irradiating body 231 and a reflecting unit 232. The irradiating body 231 is fitted with an illumination 233 and a first mirror 234. The illumination 233 has a longitudinal direction which lies in a direction (width direction) perpendicular to the X-directions indicated by arrows and Z-directions indicated by arrows. The illumination 233 irradiates the flexible printed board 100 with light. The first mirror 234 reflects the light that has been emitted from the illumination 233 and reflected by the flexible printed board 100 toward the second mirror 235.

The reflecting unit 232 also includes a second mirror 235 and a third mirror 236. The reflecting unit 232, using the second mirror 235, reflects the light reflected by the first mirror 234 so as to be aligned in the direction Z2 indicated by arrow. Further, the reflecting unit 232, using the third mirror 236, reflects the light reflected by the second mirror 235 to travel in the direction of X2 indicated by arrow.

The data conversion unit 24 includes an imaging lens 241 and an image sensor 242. The imaging lens 241 images the reflected light (optical image) on the image sensor 242. The image sensor 242 is configured from light-receiving elements, such as Charge Coupled Devices (CCD) or Contact Image Sensors (CIS), arranged along the longitudinal direction at a predetermined pixel density. The image sensor 242 generates and accumulates charge corresponding to the amount of light received the optical image, and outputs the charge in the form of an electric signal.

When the CISs are used as the light-receiving elements of the image sensor 242, the above-described various mirrors 234 to 236 may be omitted, and the imaging lens 241 may also be omitted.

In FIG. 3, the substrate reading device 20 has a configuration similar to a flat-head type scanner. The substrate reading device 20, however, may be of other types, such as a type in which the flexible printed board 100 can be fed automatically (sheet-feed type).

The lid 25 is a lid member rotatably attached to the housing 21. The lid 25 has a white reflecting plate 251 attached thereto, for example. The white reflecting plate 251 is disposed so as to cover the photographing base 212 when the lid 25 is closed.

The control unit 26 is a unit which controls the drive timing and the like of the image sensor 242. The control unit 26 is also a unit which forms image data by processing an analog signal output from the image sensor 242.

The interface 27 is a unit which reads information supplied from an external device, such as the computer 30, by converting the representation format of the information into an internal format. The interface 27 is also a unit which outputs the image data formed by the control unit 26 to the outside, such as the computer 30, in the form of a signal of a predetermined format.

<2-2. Computer>

Figure 4:
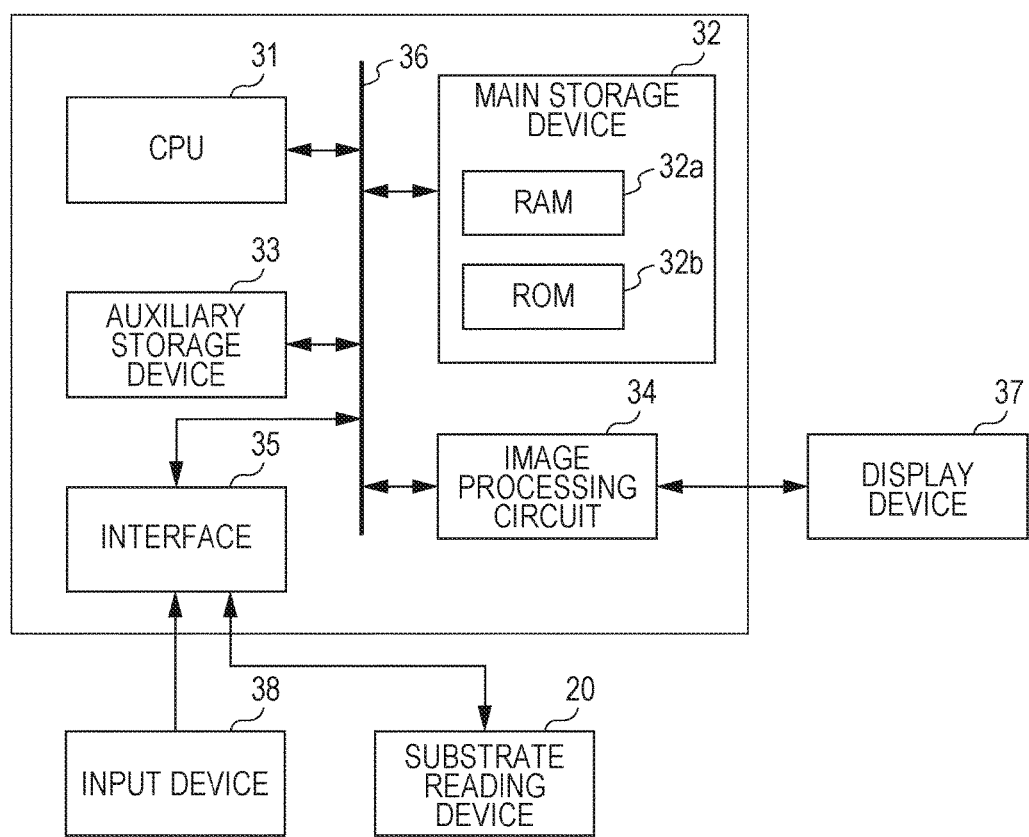
FIG. 4 is a block diagram illustrating a configuration of a computer according to the embodiment of the present invention.

The configuration of the computer 30 will be described. The computer 30 is connected to the substrate reading device 20 via a cable or a network. The computer 30 is configured as illustrated in FIG. 4. FIG. 4 is a block diagram illustrating the configuration of the computer 30.

As illustrated in FIG. 4, the computer 30 includes, as major constituent elements, a Central Processing Unit (CPU) 31, a main storage device 32, an auxiliary storage device 33, an image processing circuit 34, an interface 35, a bus 36, a display device 37, and an input device 38.

The CPU 31 is a unit which executes various computing processing in accordance with programs stored in the main storage device 32 and the auxiliary storage device 33. The CPU 31 is also a unit which controls the operation of the substrate reading device 20 and other devices.

The main storage device 32 is a storage device which the CPU 31 can directly access, such as a ROM 32a and a RAM 32b. The ROM 32a is a memory in which basic programs to be executed by the CPU 31 and data are stored. The RAM 32b is a memory in which a program being executed by the CPU 31 and data being computed, for example, are temporarily stored.

The auxiliary storage device 33 is a recording device provided with a recording medium, such as a hard disk or a flash memory. The auxiliary storage device 33, in accordance with a request from the CPU 31, reads data or a program recorded in the recording medium. The auxiliary storage device 33 further records data generated as a result of a computing processing performed by the CPU 31 in the recording medium.

The image processing circuit 34 is provided with a video memory and the like. The image processing circuit 34 executes a drawing processing based on a drawing command supplied from the CPU 31, converts resultant image data into a video signal, and supplies the video signal to the display device 37. When a Graphics Processing Unit (GPU) is used as the image processing circuit 34, for example, faster parallel computing speed may be achieved compared with the CPU 31. However, the CPU 31 may be used for computations without a GPU.

The interface 35 is a unit which reads information supplied from devices such as the input device 38 and the substrate reading device 20 by converting the representation format of the information into an internal format. As the interface 35, an interface of various standards, such as Universal Serial Bus (USB), may be used.

The bus 36 includes signal lines which interconnect the CPU 31, the main storage device 32, the auxiliary storage device 33, the image processing circuit 34, and the interface 35 to enable data exchange among them.

The display device 37 is a device which displays an image corresponding to a video signal output from the image processing circuit 34, such as a Liquid Crystal Display (LCD) monitor or a Cathode Ray Tube (CRT) monitor. The input device 38 is an input device such as a keyboard and mouse for generating and outputting information in accordance with a user operation.

<2-3. Function Block and Processing Flow>

Figure 5:
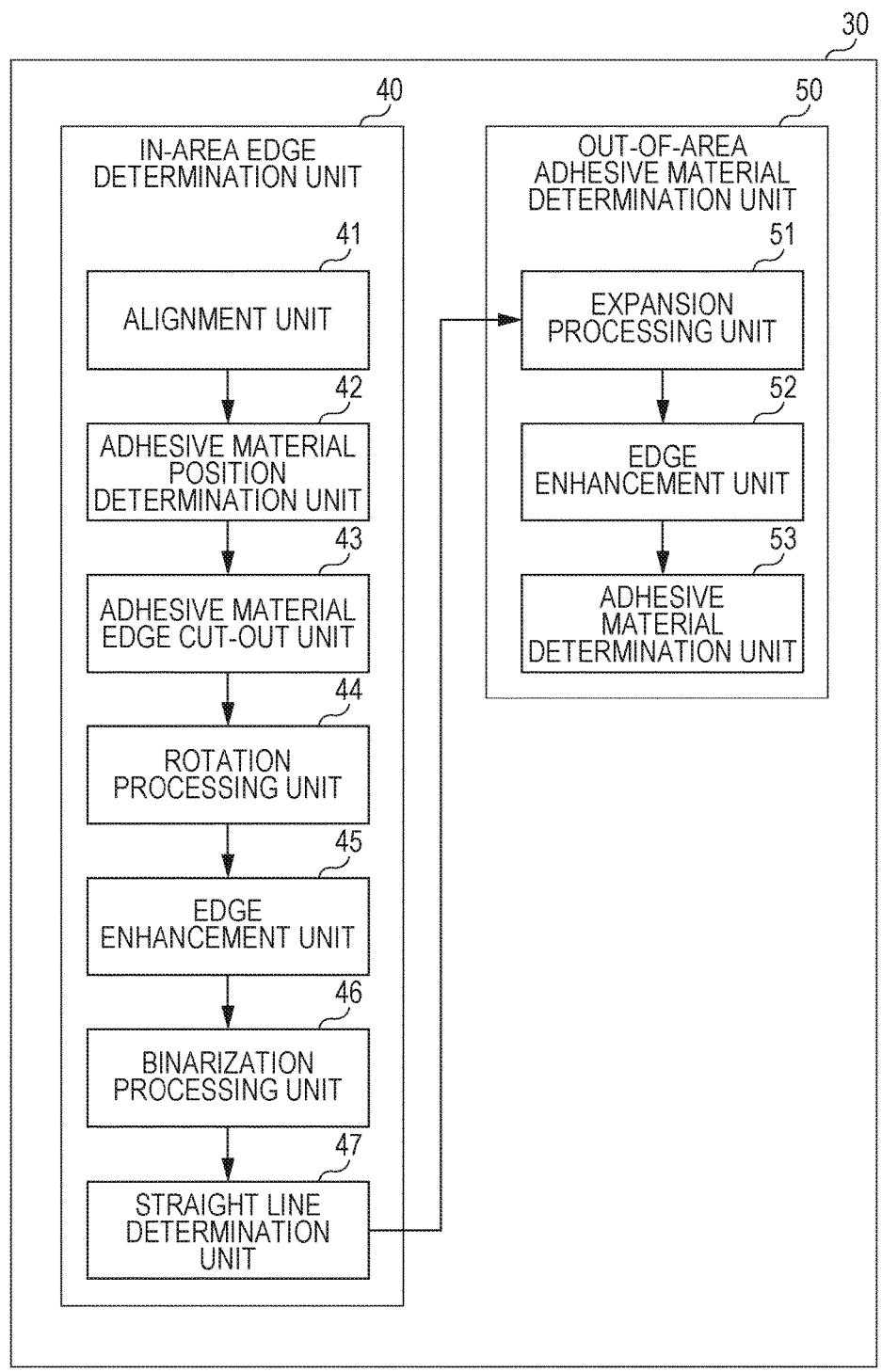
FIG. 5 is a diagram of function blocks for performing image processing on image data transmitted from a substrate reading device when, in accordance with the embodiment of the present invention, the image data are input to the computer.

By the cooperation of hardware including the CPU 31 and software and/or data stored in the main storage device 32 and the auxiliary storage device 33, and optionally with the addition of a circuit or constituent elements for executing specific processing, the configuration illustrated in the diagram of FIG. 5 is functionally implemented. FIG. 5 is a functional block diagram of image processing performed on image data transmitted from the substrate reading device 20 and input to the computer 30.

Referring to FIG. 5, the computer 30 in function block diagram includes the major constituent elements of an in-area edge determination unit 40, and an out-of-area adhesive material determination unit 50. The in-area edge determination unit 40 is a unit for determining whether the contour (edge) of the transparent adhesive material 130 is present in a correct area. The out-of-area adhesive material determination unit 50 is a unit for determining whether the contour (edge) of the transparent adhesive material 130 is present outside the correct area, and whether foreign matter is attached.

Specifically, the in-area edge determination unit 40 includes an alignment unit 41, an adhesive material position determination unit 42, an adhesive material edge cut-out unit 43, a rotation processing unit 44, an edge enhancing unit 45, a binarization processing unit 46, and a straight line determination unit 47. The out-of-area adhesive material determination unit 50 includes an expansion processing unit 51, an edge enhancing unit 52, and an adhesive material determination unit 53.

Figure 6:
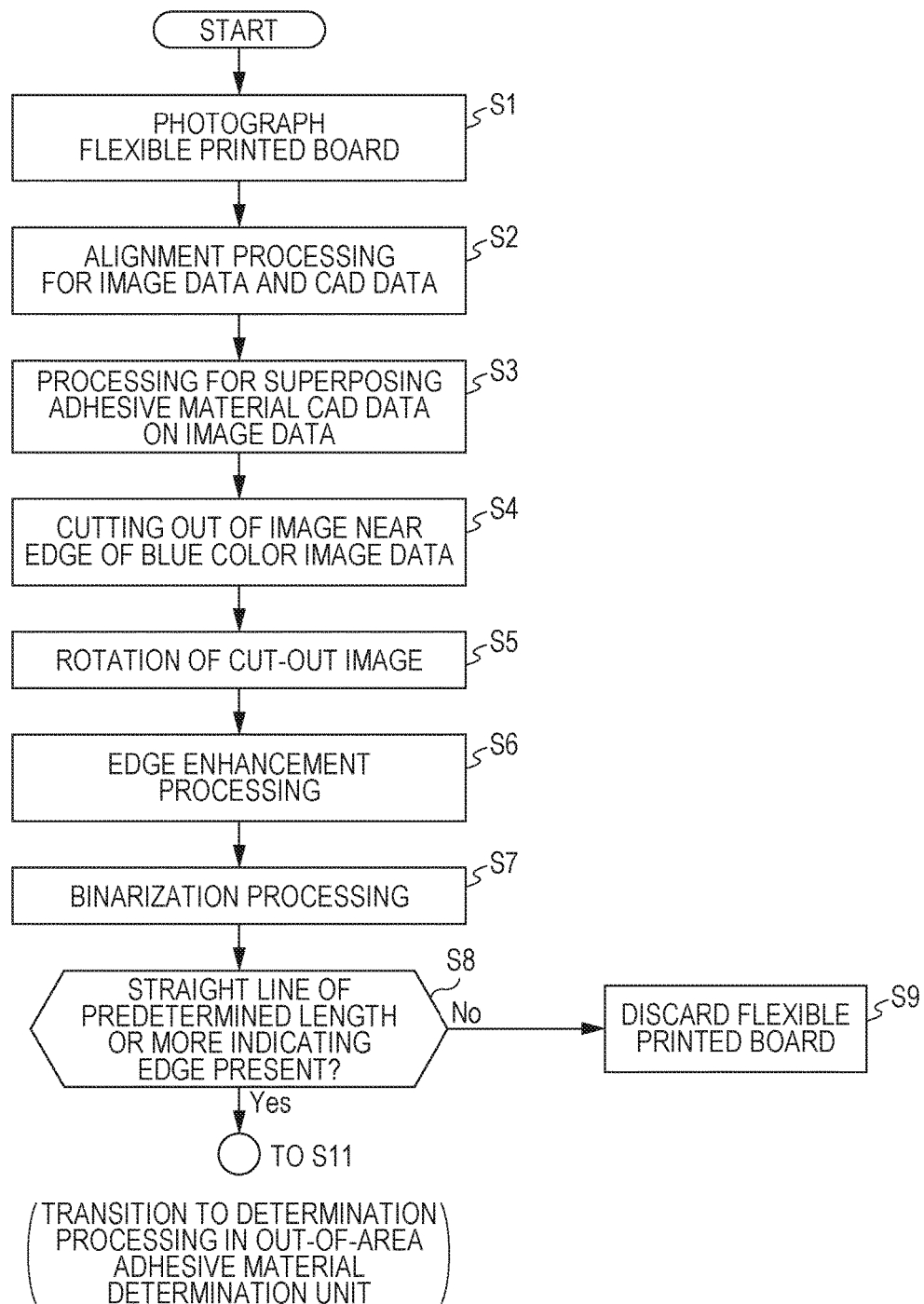
FIG. 6 is a diagram of a processing flow in an in-area edge determination unit according to the embodiment of the present invention.

In the following description, the order of description of the blocks follows the order of processing when an inspection is performed on the flexible printed board 100. Accordingly, in the following description, the processing flow of FIG. 6 will also be described. FIG. 6 illustrates the processing flow in the in-area edge determination unit 40. The processing flow of FIG. 6 includes processing at a different portion from the configuration of the function block (processing on the substrate reading device 20 side). Accordingly, the parts of FIG. 6 that are processed on the substrate reading device 20 will be described first.

(S1: Photographing of Flexible Printed Board)

The flexible printed board 100 is placed on the photographing base 212, and the lid 25 is closed. Then, the flexible printed board 100 is irradiated with light from the irradiating body 231. The flexible printed board 100 is then photographed. An electric signal from the image sensor 242 is output via an image processing unit 262 and an interface 263 to the computer 30 as image data.

(S2: Alignment Processing for Image Data and CAD Data; Corresponds to Substrate Reading Step)

After step S1, the alignment unit 41 performs an alignment processing based on the image data output from the image sensor 242 and CAD data ("CAD data C1") for the circuit pattern 120. Specifically, the base member 110 made of polyimide material absorbs most of blue light. Accordingly, if based solely on the image data for B (blue) of 256 shades of grey image data including the three primary colors of R (red), G (green), and B (blue) output from the image sensor 242, the grey level for B (blue) may become close to zero due to the absorption of blue light by the base member 110. As a result, almost black image data may be obtained, making it impossible to recognize the pattern shape of the circuit pattern 120.

Accordingly, in the alignment unit 41, of the 256 shades of grey image data including the three primary colors of R (red), G (green), and B (blue), the pattern shape of the circuit pattern 120 is recognized based on the image data ("image data G1") of either the image data for R (red), the image data for G (green), or the image data including all of R, G, and B (red, green, and blue). In the alignment unit 41, the CAD data C1 for pattern shape is aligned in accordance with the pattern shape.

In this case, the image data G1 based on the actual circuit pattern 120 is normally inclined in each of the X-Y coordinates with respect to the pattern shape CAD data C1. In addition, the image data G1 often has expansion or contraction caused in the X-direction or expansion or contraction caused in the Y-direction in. In the alignment unit 41, on the image data G1, a shape search for the CAD data C1 is performed, and coordinate conversion for aligning the CAD data with the image is calculated.

(S3: Processing for Superposing Adhesive CAD Data on Image Data; Corresponds to Adhesive Material Position Determination Step)

After the processing of step S2, the adhesive material position determination unit 42 determines the position of the CAD data for adhesive material ("adhesive material CAD data C2") with respect to the image data for B (blue) ("blue color image data G2"), and performs a superposition processing after the position is determined. Specifically, as the adhesive material CAD data C2, data that has already been aligned with respect to the pattern shape CAD data C1 is prepared. Accordingly, as a formula for coordinate conversion between the image data G1 and the pattern shape CAD data C1 is determined in step S2, the adhesive material CAD data C2 can be superposed on the blue color image data G2. As the adhesive material CAD data C2 is superposed on the blue color image data G2, contour data is formed, which is referred to as adhesive material alignment data C3.

(S4: Cutting Out of Blue Color Image Data Near Edge)

After the processing of step S3, the adhesive material edge cut-out unit 43 performs processing for cutting out the blue color image data G2 in a predetermined area including an edge of the adhesive material alignment data C3. The cutting out involves cutting out a predetermined length or more of a straight line portion of the blue color image data G2. The portion thus cut out will be hereafter referred to as a cut-out image K1. The cut-out image K1 is obtained with regard to a straight line edge of the adhesive material alignment data C3. The cutting out is implemented such that the straight line edge of the adhesive material alignment data C3 becomes parallel with a long side of the cut-out image K1. Accordingly, in the stage where the cut-out image K1 is formed, it is rarely the case that the angle of the long side of the cut-out image K1 is vertical or vertical with respect to the X-axis and Y-axis of the X-Y coordinates system. The long side of the cut-out image K1 may form various angles with respect to the X-axis and Y-axis.

The cut-out image K1 has a predetermined length of approximately 10 mm, for example. The length, however, may be set to any numerical value. Accordingly, from the adhesive material alignment data C3 in which the adhesive material CAD data C2 is superposed, several tens of cut-out images K1 may be formed.

During the cutting-out, it is possible to cut out, when the edge of the adhesive material alignment data C3 is disposed at the center, the blue color image data G2 in which the adhesive material alignment data C3 is superposed within a tolerance range of the edge disposed at the center. The tolerance range is ±0.5 mm with respect to the edge, for example. The tolerance range may have other numerical values. A range outside a tolerance may also be employed. Depending on the color tone of the material of interest, the image data G1 or the like may be cut out instead of the blue color image data G2.

(S5: Rotation of Cut-Out Image)

The rotation processing unit 44 next performs a rotation processing for all of the cut-out images K1 that have been cut out. A rotated image will be referred to as a cut-out rotation image K2. In the rotation processing, a conversion for rotating the cut-out image K1 such that the long side of the cut-out rotation image K2 becomes horizontal or vertical with respect to a reference coordinate axis (such as the X-axis or Y-axis) is implemented using image processing software and the like. The implementation of the rotation processing facilitates an edge enhancement processing which will be described below. In practice, the cutting-out and rotating of an image may be performed simultaneously.

(S6: Edge Enhancement Processing)

The edge enhancing unit 45 then performs, with respect to the cut-out rotation image K2 after the rotation processing, a filter processing for enhancing the edge (contour) of adhesive material present in the horizontal direction or vertical direction with respect to the reference coordinate axis (the X-axis or Y-axis of the X-Y coordinates). Examples of the filter processing include an unsharp mask processing and Sobel. As an edge enhancement processing, an unsharp mask processing is known which determines a difference between a smoothed image and an original image. Generally, smoothing in the X- and Y-directions is implemented. However, because the direction of the edge is known, the edge may be more clearly enhanced by smoothing only in a direction perpendicular to the edge. The edge enhancement processing performed on the cut-out image K1 creates edge enhanced data in which the edge of the transparent adhesive material 130 is enhanced. The edge enhanced data will be described in the following with reference to a cut-out edge enhanced image K3.

(S7: Binarization Processing; Corresponds to Binarization Processing Step)

The binarization processing unit 46 next forms binarization data K4 by performing a binarization processing on the cut-out edge enhanced image K3 after the edge enhancement processing. The binarization processing may include a hysteresis binarization processing. In hysteresis binarization, two types of threshold values are used. Hysteresis binarization is a method whereby pixels with large contrast are extracted using a first threshold value, and adjacent pixels with small contrast are extracted using a second threshold value. With the hysteresis binarization method, an image with a poor S/N can be more easily binarized than by simple binarization.

(S8: Straight Line Determination Processing; Corresponds to Straight Line Determination Step)

The straight line determination unit 47 next performs a straight line determination processing on the binarization data K4 after the binarization processing. In the straight line determination processing, it can be determined, by performing the Hough transform, for example, whether there is a straight line in the binarization data K4 indicating an edge.

When the Hough transform is performed, if straight lines of each and every angle were to be determined, the processing time would become long. In the present embodiment, it is only necessary to detect, through the rotation processing of step S5, the edge (contour) of the adhesive in a state close to being horizontal or vertical. In the present embodiment, it is only necessary to process the five straight lines consisting of a straight line forming an angle of zero degree; straight lines forming angles of ±0.5 degrees; and straight lines forming angles of ±1 degree with respect to the horizontal or vertical. Accordingly, even without a ρ–θ transform of the Hough transform, and even if pixels are counted by drawing a virtual line on the XY coordinates, processing can be performed at a sufficient speed. Generally, voting in the Hough transform is performed based on binary image data. However, it is also possible to set finer detection threshold values by performing voting based on grey-value, instead of binary, image data.

The straight lines to be determined, however, are not limited to the aforementioned five. For example, the determination may be implemented based on only one straight line of zero degree. The determination may be implemented based on a straight line of zero degree and straight lines of other angles (such as ±0.5 degrees or ±1 degree). The determination may also be implemented based not on the straight line of zero degree but on the straight lines of other angles.

With regard to the above-described compulsorily drawn straight line, when there is a straight line such that, with respect to the length of the long side of the cut-out rotation image K2, or the length of an ideal straight line, so to speak, the ratio of pixels indicating the presence of an edge is greater than or equal to a predetermined ratio, such as 30%, it is determined that there is the edge (contour) of the adhesive material. The numerical value of the predetermined ratio may be set to any numerical value other than 30%.

As a result of the determination, if it is determined that there is the edge (contour) of the adhesive material (Yes in step S8 of FIG. 6), it is determined that proper application was achieved in a predetermined area including the edge of adhesive material. In this case, transition to a determination processing in the out-of-area adhesive material determination unit 50, which will be described later with reference to FIG. 7, for example, takes place. Conversely, if it is determined that the edge (contour) of the adhesive material is absent (No in step S8 of FIG. 6), it is determined that the adhesive material is not properly applied. With regard to the flexible printed board 100 thus determined, the downstream steps are not implemented, and the flexible printed board 100 is discarded. The discarding corresponds to step S9 in FIG. 6. The above is the processing performed by the in-area edge determination unit 40.

Figure 7:
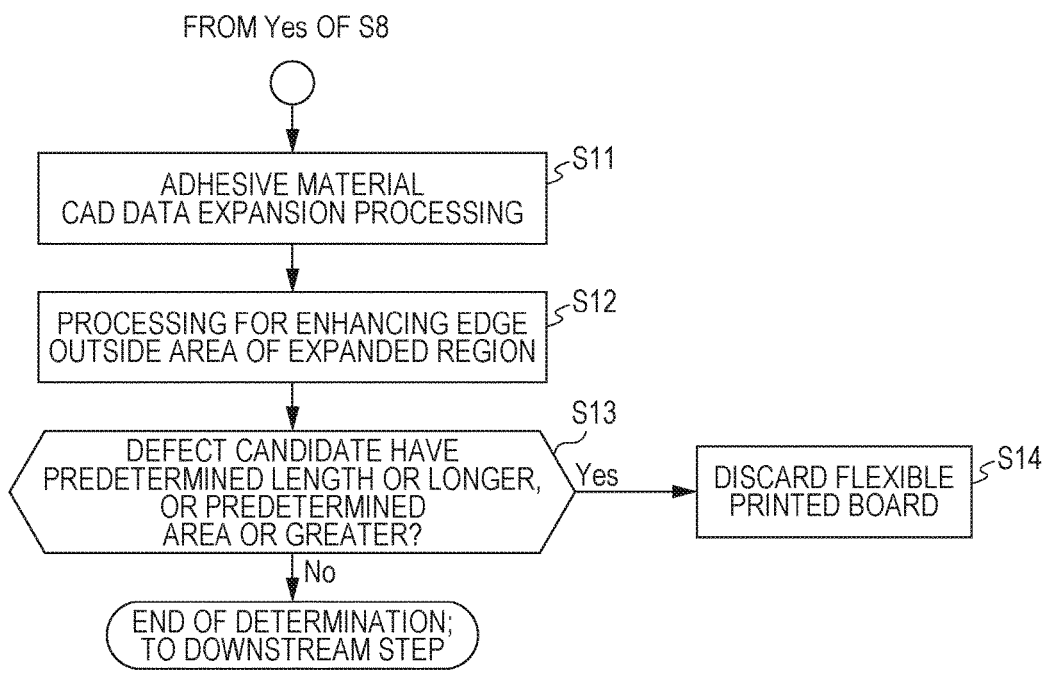
FIG. 7 is a diagram of a processing flow in an out-of-area adhesive material determination unit according to the embodiment of the present invention.

In the following, the configurations of the out-of-area adhesive material determination unit 50, and processing performed by each of the configurations will be described. In the out-of-area adhesive material determination unit 50, it is determined whether the edge (contour) of the transparent adhesive material 130 is present outside the correct area, and whether foreign matter is attached. FIG. 7 illustrates a processing flow in the out-of-area adhesive material determination unit 50.

(S11: Expansion Processing; Corresponds to Expansion Processing Step)

First, with respect to the adhesive material alignment data C3 obtained by superposing the CAD data C2 for adhesive material on the B (blue) image data G2 as described above in step S3, the expansion processing unit 51 performs an expansion processing on the adhesive material alignment data C3. In the expansion processing, the sides of the element data of each adhesive material of the adhesive material alignment data C3 are processed so as to be expanded outward just by a predetermined size. In this way, the area of the adhesive material alignment data C3 is placed in a state of being expanded in every direction just by a predetermined size.

The expansion processing has the following purpose. When the adhesive material is normally attached, the edge (contour) of the adhesive material is normally present inside the expanded portion of the element data of each adhesive material. If the edge (contour) of the adhesive material is detected outside the expanded portion of the element data, or if another portion that should not be present is detected, this may indicate an adhesive material application error, or the presence of something other than adhesive material, such as dust.

Accordingly, in order to facilitate the determination of a portion suspected of being foreign matter, the above-described expansion processing is performed. In the following, the region formed by the expansion processing will be referred to as a mask region M1.

(S12: Edge Enhancement Processing; Corresponds to Edge Enhancement Step)

Next, the edge enhancing unit 52 performs an edge enhancement processing on the image data outside the area of the mask region M1. The edge enhancement processing is similar to the processing of step S6. In step S6, however, the edge (contour) of the adhesive material which is present in a horizontal direction or vertical direction with respect to the X-axis or Y-axis is enhanced. In contrast, in the present step, the edge enhancement processing is performed in a state having no directionality. Specific examples of the processing include an unsharp masking processing and Sobel, as in step S6.

In the present embodiment, the edge enhancement processing also includes a binarization processing similar to the one described in step S7. Hereafter, the image data with an enhanced edge will be referred to as edge enhanced image G5. The edge enhanced image G5 is binarized by the above-described hysteresis binarization. In this state, the line of the edge of adhesive material may be intermittent and not continuous. In order to distinguish from a noise component, a binarization region expansion processing is performed to make the line continuous. At this point in time, the noise component is also expanded. However, by setting appropriate parameters of area, length and the like, the edge of adhesive material can be extracted. As a result of the above-described processing, if there is the edge of adhesive material outside the mask region M1, it is determined that there is a defect, and the flexible printed board 100 is discarded and the subsequent steps are not implemented.

(S13: Processing for Determining Adhesive Material Outside the Area of the Mask Region; Corresponds to Adhesive Material Determination Step)

Next, the adhesive material determination unit 53 performs processing for determining whether adhesive material or foreign matter is present outside the area of the mask region M1. If it is determined that there is foreign matter, the flexible printed board 100 is determined to be defective and discarded without implementing the subsequent steps. The discarding corresponds to step S14 in FIG. 7. If a defect candidate is smaller than a predetermined length and smaller than a predetermined area, the flexible printed board 100 is determined to be normal, and the subsequent steps are implemented.

The predetermined length is 9 mm, for example, and the predetermined area is 2 mm$^2$, for example. However, the value of the predetermined length and the value of the predetermined area may be set to any values.

3. Effects

According to the substrate inspection device 10 and the substrate manufacturing method described above, in the substrate reading device 20, the flexible printed board 100 is irradiated with visible light, and image data of the flexible printed board 100 are acquired. In the adhesive material position determination unit 42, the position of the adhesive material CAD data C2 corresponding to the transparent adhesive material 130 with respect to the blue color image data G2 among the image data corresponding to the blue light, which is easily absorbed by polyimide, is determined. In addition, the edge enhancing unit 45 performs, on the image data including at least the blue color image data G2, the processing for enhancing the edge of the transparent adhesive material 130. In the straight line determination unit 47, based on the edge enhanced data in which the edge of the transparent adhesive material 130 has been enhanced, it is determined whether the edge of the transparent adhesive material 130 is present in the edge enhanced data.

In this case, the base member 110 made of polyimide material absorbs blue light. Accordingly, when the blue color image data G2 is used for the detection of the contour (edge) of the transparent adhesive material 130, the pattern shape of the circuit pattern 120 on the back surface of the base member 110 made of polyimide material disappears, while the light scattered (reflected) by the contour (edge) of the transparent adhesive material 130 on the front surface of the base member 110 made of polyimide material is left without being absorbed. Accordingly, the use of the blue color image data G2 facilitates the detection of scattered light at the edge. By forming the adhesive material alignment data C3 using the blue color image data G2 and also the adhesive material CAD data C2, the position of the edge of the transparent adhesive material 130 can be roughly identified, thereby facilitating the processing of enhancing the edge of the transparent adhesive material 130. After edge enhancement, in the straight line determination unit 47, it is determined whether the edge of the transparent adhesive material 130 is present. In this way, the edge of the transparent adhesive material 130 can be satisfactorily detected.

Thus, with the relatively simple configuration including the substrate reading device 20 and the computer 30, it can be satisfactorily determined whether the transparent adhesive material 130 is properly applied to the base member 110.

Compared with the case where an operator visually determines whether the transparent adhesive material 130 is normally applied, it is possible to determine whether the application is normal consistently and accurately. In addition, because the substrate reading device 20 has a configuration similar to that of a scanner, the cost of the substrate inspection device 10 can be kept inexpensive.

In the present embodiment, the binarization processing unit 46 forms the binarization data K4 by performing a binarization processing on the edge enhanced data in which the edge of the transparent adhesive material 130 has been enhanced by the edge enhancing unit 45. Based on the binarization data K4, the straight line determination unit 47 determines whether the edge of the transparent adhesive material 130 is present. In this way, the processing load can be decreased compared with a determination based on a grey image, and the processing speed can be increased.

In the present embodiment, after the position determination by the adhesive material position determination unit 42, the adhesive material edge cut-out unit 43, based on the adhesive material alignment data C3 obtained by superposing the adhesive material CAD data C2 on the blue color image data G2, cuts out image data in an area of a predetermined distance from the edge of the adhesive material CAD data C2, forming the cut-out image K1. The edge enhancing unit 45, based on the cut-out image K1, performs processing for enhancing the edge of the transparent adhesive material 130.

The forming of the cut-out image K1 makes it possible to cut out an ideal image near the adhesive edge position, whereby straight line detection can be performed in a limited area. Accordingly, a strict threshold value can be set even for an adhesive edge that is hard to see, and detection accuracy can be increased. It also becomes possible to decrease the processing load in the edge enhancement processing. The formation of the cut-out image K1 also makes it possible for the straight line determination unit 47 to more reliably determine the presence of the edge of the transparent adhesive material 130.

Further, in the present embodiment, the rotation processing unit 44 rotates the cut-out image K1 formed by the adhesive material edge cut-out unit 43 so that the long side of the cut-out image K1 which is parallel or vertical with respect to the edge of the adhesive material CAD data C2 becomes horizontal or vertical with respect to the reference coordinate axis (such as the X-axis or the Y-axis). Based on the cut-out image K1 after the rotation processing, the edge enhancing unit 45 performs processing for enhancing the edge of the transparent adhesive material 130.

Accordingly, when the edge enhancement processing is performed based on the cut-out image K1 after the rotation processing, the edge enhancement processing is performed with directionality. By performing the edge enhancement processing having directionality, the clearness of the edge of the transparent adhesive material 130 increases, and the reliability of the determination by the straight line determination unit 47 can be increased. In addition, by aligning the edge direction by performing the rotation processing, the edge enhancement processing can be implemented with directionality, and the edge of adhesive material can be made clear.

According to the present embodiment, the straight line determination unit 47 determines by the Hough transform whether a straight line corresponding to the edge of the transparent adhesive material 130 is present. In addition, after the straight line is detected, if there are pixels having pixel values indicating an edge is present on the straight line by a predetermined ratio or more, it is determined that the edge of the transparent adhesive material 130 is present. By performing the Hough transform, the straight line corresponding to the edge of the transparent adhesive material 130 can be easily detected. Because it is determined whether the pixels having the pixel values indicating an edge are present on the detected straight line by a predetermined ratio or more, the determination of the presence or absence of the edge of the transparent adhesive material 130 is facilitated.

In addition, according to the present embodiment, in the substrate reading device 20, the flexible printed board 100 is irradiated with visible light and the image data of the flexible printed board 100 are acquired. In the adhesive material position determination unit 42, with respect to the blue color image data G2, among the image data, corresponding to the blue light, which is readily absorbed by polyimide, the position of the adhesive material CAD data C2 corresponding to the transparent adhesive material 130 is determined. After the determination, the adhesive material alignment data C3 in which the adhesive material CAD data is superposed is created. In the expansion processing unit 51, processing for expanding the sides of the element data of each transparent adhesive material 130 in the adhesive material CAD data C2 outward just by a predetermined size is performed. In the edge enhancing unit 52, a binarization processing is performed on an expanded region G4 after the expansion processing while enhancing the edge of the transparent adhesive material 130 or foreign matter, whereby the edge of the transparent adhesive material, or the edge of foreign matter is extracted.

In the adhesive material determination unit 53, based on the edge enhanced data G5 in which the edge of the transparent adhesive material 130 or foreign matter has been enhanced by the edge enhancing unit 52, it is determined whether the edge of the transparent adhesive material 130 or the edge of foreign matter is present outside the area expanded by the expansion processing unit 51.

In this way, as in the detection of the edge of the transparent adhesive material 130 in the straight line determination unit 47, it becomes possible to easily determine whether there is an application error of the transparent adhesive material 130 being applied outside the area expanded by the expansion processing unit 51 in the element data corresponding to each adhesive material of the adhesive material CAD data C2, and whether dust and the like other than the transparent adhesive material 130 is present outside the area.

4. Modification

While an embodiment of the present invention has been described, the present invention may include other various modifications as will be described below.

In the foregoing embodiment, a pattern shape in the circuit pattern 120 is used as the alignment reference. However, the alignment reference may not be a pattern shape in the circuit pattern 120. For example, alignment marks may be formed at two locations at least of the four corners of the flexible printed board 100, and the marks may be used as alignment references.

The alignment marks may include a punched hole formed on the flexible printed board 100, for example. When a punched hole is used as the alignment mark, the edge of the transparent adhesive material 130 can be detected even with respect to a single-color image in which only the edge of the transparent adhesive material 130 appears as a density difference.

The edge of the transparent adhesive material 130 may be detected using a technique different from the embodiment. For example, when a polarizing filter is used and an image of reflected light from an illumination is captured by an image sensor and the like in a state such that the Brewster's angle is formed, irregularities on the surface of the flexible printed board 100 can be satisfactorily detected by performing the imaging using the polarizing filter. Accordingly, it becomes possible to satisfactorily detect the edge of the transparent adhesive material 130 present on the surface of the flexible printed board 100. In this case, the edge of the transparent adhesive material 130 may be detected in a more satisfactory manner by applying the technique according to any of the image processes described with reference to the foregoing embodiment.

In another technique, blue light may be used and image-captured in a state of being specularly reflected so as to detect irregularities on the surface of the flexible printed board 100. In this case, too, by satisfactorily detecting irregularities on the surface of the flexible printed board 100, it becomes possible to satisfactorily detect the edge of the transparent adhesive material 130 which is present on the surface of the flexible printed board 100.

In another technique, the transparent adhesive material may be colored. In this case, visual recognition of the color facilitates the recognition of the presence or absence of the transparent adhesive material 130.

In another technique, the transparent adhesive material may be formed in a state including a fluorescence-emitting component, the transparent adhesive material may be irradiated with ultraviolet light, and an image of the irradiated state may be captured.

In the foregoing embodiment, the substrate inspection device 10 includes the movable member 22 moveably provided in the housing 21. The movable member 22 is provided with the irradiating body 231 including the illumination 233; the reflecting unit 232; and the data conversion unit 24 including the image sensor 242. These, however, may be configured to be separately provided.

The substrate inspection device 10 may also be configured to only perform the processing in the in-area edge determination unit 40, or may be configured to only perform the processing in the out-of-area adhesive material determination unit 50. The straight line determination processing in step S8 may be performed using a grey image without performing the binarization processing in step S7. When the straight line determination processing is performed using a grey image, a sum of pixel values of a grey image positioned on a virtual straight line (including a virtual straight line in either the horizontal direction, vertical direction, or inclined direction) may be computed for predetermined pixels, and it may be determined whether the pixel value for the predetermined pixels exceeds a threshold value.

In the foregoing embodiment, the adhesive material alignment data C3 as a whole may be used without performing the processing in step S4 to cut out the adhesive material alignment data C3 in the predetermined area of the adhesive material CAD data C2 including an edge. The cut-out image K1 rotation processing in step S5 may not be performed. In step S12, the binarization processing may not be performed.

In the foregoing embodiment, in the Hough transform in step S8, rather than just for a straight line, similar processing may be performed with respect to a circle or other curves. In the foregoing embodiment, the cut-out image K1 is rotated such that the long side of the cut-out image K1 becomes horizontal or vertical with respect to a reference coordinate axis (such as the X-axis or Y-axis), and thereafter the edge enhancement processing is performed. However, the rotation processing for the cut-out image K1 may be performed such that the long side of the cut-out image K1 is inclined by 45 degrees with respect to a reference coordinate axis (such as the X-axis or Y-axis). In this way, too, the edge enhancement processing can be satisfactorily performed.

In the foregoing embodiment, the object to be inspected by the substrate inspection device is a flexible printed board including a base member made of polyimide material to which transparent adhesive material is applied. The object to be inspected, however, is not limited to an object to which transparent adhesive material is applied. The object to be inspected may include an object including a base member to which a hard-to-see transparent material is applied. In this case, the transparent material may be other than transparent adhesive material.

DESCRIPTION OF REFERENCE SIGNS

10 Substrate inspection device
20 Substrate reading device
21 Housing
22 Movable member
23 Optical unit
24 Data conversion unit
25 Lid
26 Control unit
27 Interface
30 Computer
31 CPU
32 Main storage device
32a ROM
32b RAM
33 Auxiliary storage device
34 Image processing circuit
35 Interface
36 Bus
37 Display device
38 Input device
40 In-area edge determination unit
41 Alignment unit
42 Adhesive material position determination unit
43 Adhesive material edge cut-out unit
44 Rotation processing unit
45 Edge enhancing unit
46 Binarization processing unit
47 Straight line determination unit
50 Out-of-area adhesive material determination unit
51 Expansion processing unit
52 Edge enhancing unit
53 Adhesive material determination unit
100 Flexible printed board
110 Base member
120 Circuit pattern
130 Transparent adhesive material
211 Opening portion
212 Photographing base
231 Irradiating body
232 Reflecting unit
233 Illumination
234 First mirror
235 Second mirror
236 Third mirror
241 Imaging lens
242 Image sensor
251 Reflecting plate

The invention claimed is:

1. A substrate inspection device for inspecting a flexible printed board comprising a base member made of polyimide material and a transparent adhesive material applied thereto to determine whether the transparent adhesive material is properly applied, the substrate inspection device comprising:
a substrate reading device that irradiates the flexible printed board with visible light to acquire image data of the flexible printed board;
an adhesive material position determination unit that determines a position of adhesive material CAD data corresponding to the transparent adhesive material, with respect to blue color image data among the image data corresponding to blue light that is readily absorbed by the polyimide;
an edge enhancing unit that performs processing, on image data including at least the blue color image data, to enhance an edge of the transparent adhesive material; and
a straight line determination unit that determines whether, based on edge enhanced data in which the edge of the transparent adhesive material has been enhanced by the edge enhancing unit, the edge of the transparent adhesive material is present in the edge enhanced data.

2. The substrate inspection device according to claim 1, comprising a binarization processing unit that creates binary image data by performing binarization processing on the edge enhanced data in which the edge of the transparent adhesive material has been enhanced by the edge enhancing unit,
wherein the straight line determination unit determines whether, based on the binary image data, the edge of the transparent adhesive material is present.

3. The substrate inspection device according to claim 2, comprising an adhesive material edge cut-out unit that forms a cut-out image by, after the position determination by the adhesive material position determination unit, cutting out image data in an area of a predetermined distance from an edge of the adhesive material CAD data, based on adhesive material alignment data in which the adhesive material CAD data is superposed on the blue color image data,
wherein the edge enhancing unit performs processing to enhance the edge of the transparent adhesive material based on the cut-out image.

4. The substrate inspection device according to claim 3, comprising a rotation processing unit that rotates the cut-out image formed by the adhesive material edge cut-out unit so that a long side of the cut-out image which is parallel or vertical with respect to the edge of the adhesive material CAD data becomes horizontal or vertical with respect to a reference coordinate axis, wherein the edge enhancing unit performs processing to enhance the edge of the transparent adhesive material based on the cut-out image after the rotation processing.

5. The substrate inspection device according to claim 4, wherein the straight line determination unit detects, by the Hough transform, whether a straight line corresponding to the edge of the transparent adhesive material is present, and, after the straight line detection, determines that the edge of the transparent adhesive material is present if pixels having a pixel value indicating an edge are present on the straight line by a predetermined ratio or more.

6. The substrate inspection device according to claim 3, wherein the straight line determination unit detects, by the Hough transform, whether a straight line corresponding to the edge of the transparent adhesive material is present, and, after the straight line detection, determines that the edge of the transparent adhesive material is present if pixels having a pixel value indicating an edge are present on the straight line by a predetermined ratio or more.

7. The substrate inspection device according to claim 2, wherein the straight line determination unit detects, by the Hough transform, whether a straight line corresponding to the edge of the transparent adhesive material is present, and, after the straight line detection, determines that the edge of the transparent adhesive material is present if pixels having a pixel value indicating an edge are present on the straight line by a predetermined ratio or more.

8. The substrate inspection device according to claim 1, comprising an adhesive material edge cut-out unit that forms a cut-out image by, after the position determination by the adhesive material position determination unit, cutting out image data in an area of a predetermined distance from an edge of the adhesive material CAD data, based on adhesive material alignment data in which the adhesive material CAD data is superposed on the blue color image data, wherein the edge enhancing unit performs processing to enhance the edge of the transparent adhesive material based on the cut-out image.

9. The substrate inspection device according to claim 8, comprising a rotation processing unit that rotates the cut-out image formed by the adhesive material edge cut-out unit so that a long side of the cut-out image which is parallel or vertical with respect to the edge of the adhesive material CAD data becomes horizontal or vertical with respect to a reference coordinate axis, wherein the edge enhancing unit performs processing to enhance the edge of the transparent adhesive material based on the cut-out image after the rotation processing.

10. The substrate inspection device according to claim 9, wherein the straight line determination unit detects, by the Hough transform, whether a straight line corresponding to the edge of the transparent adhesive material is present, and, after the straight line detection, determines that the edge of the transparent adhesive material is present if pixels having a pixel value indicating an edge are present on the straight line by a predetermined ratio or more.

11. The substrate inspection device according to claim 8, wherein the straight line determination unit detects, by the Hough transform, whether a straight line corresponding to the edge of the transparent adhesive material is present, and, after the straight line detection, determines that the edge of the transparent adhesive material is present if pixels having a pixel value indicating an edge are present on the straight line by a predetermined ratio or more.

12. The substrate inspection device according to claim 1, wherein the straight line determination unit detects, by the Hough transform, whether a straight line corresponding to the edge of the transparent adhesive material is present, and, after the straight line detection, determines that the edge of the transparent adhesive material is present if pixels having a pixel value indicating an edge are present on the straight line by a predetermined ratio or more.

13. A substrate inspection device for inspecting a flexible printed board comprising a base member made of polyimide material and a transparent adhesive material applied thereto to determine whether the transparent adhesive material is properly applied, the substrate inspection device comprising:
a substrate reading device that irradiates the flexible printed board with visible light to acquire image data of the flexible printed board;
an adhesive material position determination unit that determines a position of adhesive material CAD data corresponding to the transparent adhesive material with respect to blue color image data among the image data corresponding to blue light that is readily absorbed by the polyimide, and that, after the determination, creates adhesive material alignment data in which the adhesive material CAD data is superposed;
an expansion processing unit that forms a mask region by performing expansion processing to outwardly expand each side of element data of each transparent adhesive material in the adhesive material CAD data, just by a predetermined size;
an edge enhancing unit that, by performing binarization processing while enhancing an edge of the transparent adhesive material or foreign matter on the image data outside an area of the mask region, extracts the edge of the transparent adhesive material or the edge of foreign matter; and
an adhesive material determination unit that, based on edge enhanced data in which the edge of the transparent adhesive material or the foreign matter has been enhanced by the edge enhancing unit, determines whether the edge of the transparent adhesive material or the edge of foreign matter is present outside an area expanded by the expansion processing unit.

14. A substrate manufacturing method for manufacturing a flexible printed board comprising a base member made of polyimide material and a transparent adhesive material applied thereto, the method comprising:

a substrate reading step of irradiating the flexible printed board with visible light, and acquiring image data of the flexible printed board;
an adhesive material position determination step of determining a position of adhesive material CAD data corresponding to the transparent adhesive material with respect to blue color image data among the image data corresponding to blue light that is readily absorbed by the polyimide, and, after the determination, creating adhesive material alignment data in which the adhesive material CAD data is superposed;
an edge enhancement step of performing processing, on image data including at least the blue color image data, to enhance an edge of the transparent adhesive material;
a binarization processing step of extracting the edge of the transparent adhesive material by creating binary image data by performing binarization processing on an edge enhanced data in which the edge of the transparent adhesive material has been enhanced by the edge enhancing step; and a straight line determination step of determining, based on the binary image data, whether the edge of the transparent adhesive material is present in the binary image data.

15. A substrate manufacturing method for manufacturing a flexible printed board comprising a base member made of polyimide material and a transparent adhesive material applied thereto, the method comprising:

a substrate reading step of irradiating the flexible printed board with visible light, and acquiring image data of the flexible printed board;

an adhesive material position determination step of determining a position of adhesive material CAD data corresponding to the transparent adhesive material with respect to blue color image data among the image data corresponding to blue light that is readily absorbed by the polyimide, and, after the determination, creating adhesive material alignment data in which the adhesive material CAD data is superposed;

an expansion processing step of forming a mask region by performing expansion processing so as to outwardly expand each side of element data of each transparent adhesive material in the adhesive material CAD data just by a predetermined size;

an edge enhancement step of extracting, by performing binarization processing while enhancing an edge of the transparent adhesive material or foreign matter on the image data outside an area of the mask region, the edge of the transparent adhesive material or the edge of foreign matter; and an adhesive material determination step of determining, based on edge enhanced data in which the edge of the transparent adhesive material or the foreign matter has been enhanced by the edge enhancement step, whether the edge of the transparent adhesive material or the edge of foreign matter is present outside an area expanded by the expansion processing step.

* * * * *